United States Patent [19]
Connell et al.

[11] Patent Number: 6,034,115
[45] Date of Patent: *Mar. 7, 2000

[54] INDOLYL-SUBSTITUTED PHENYLACETIC ACID DERIVATIVES

[75] Inventors: Richard Connell, Trumbull, Conn.; Siegfried Goldmann; Ulrich Müller, both of Wuppertal, Germany; Stefan Lohmer, Milan, Italy; Hilmar Bischoff; Dirk Denzer, both of Wuppertal, Germany; Rudi Grützmann, Solingen, Germany; Stefan Wohlfeil, Hilden, Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/761,922

[22] Filed: Dec. 9, 1996

[30]   Foreign Application Priority Data

Dec. 15, 1995   [DE]   Germany ............................ 195 46 919

[51] Int. Cl.$^7$ ..................... A61K 31/415; C07D 235/18; C07D 235/10; C07D 235/08
[52] U.S. Cl. ......................................... 514/394; 548/309.7
[58] Field of Search ......................... 548/309.7; 514/394

[56]   References Cited

U.S. PATENT DOCUMENTS

| | | |
|---|---|---|
| 5,314,880 | 5/1994 | Whittaker et al. . |
| 5,352,687 | 10/1994 | Müller et al. . |
| 5,376,671 | 12/1994 | Müller-Gliemann et al. . |
| 5,420,149 | 5/1995 | Müller et al. . |
| 5,521,206 | 5/1996 | Müller . |
| 5,527,809 | 6/1996 | Müller-Gliemann et al. . |
| 5,776,964 | 7/1998 | Muller et al. ........................... 514/394 |

FOREIGN PATENT DOCUMENTS

| | | |
|---|---|---|
| 513533 | 11/1992 | European Pat. Off. . |
| 560162 | 9/1993 | European Pat. Off. . |
| 560163 | 9/1993 | European Pat. Off. . |
| 565986 | 10/1993 | European Pat. Off. . |
| 610698 | 8/1994 | European Pat. Off. . |

*Primary Examiner*—Patricia L. Morris
*Attorney, Agent, or Firm*—Norris, McLaughlin & Marcus, P.A.

[57]   ABSTRACT

The indolyl-substituted phenylacetic acid derivatives are prepared by reacting the corresponding phenylacetic acids with the required amines. The indolyl-substituted phenylacetic acid derivatives are suitable as active compounds in medicaments, in particular in antiarteriosclerotic medicaments.

8 Claims, No Drawings

INDOLYL-SUBSTITUTED PHENYLACETIC ACID DERIVATIVES

The present invention relates to indolyl-substituted phenylacetic acid derivatives, processes for their preparation and their use as medicaments, in particular as antiatherosclerotic medicaments.

Phenylacetic acid derivatives with heterocyclic substituents and substituted imidazo[4,5-b]pyridines and benzimidazoles are known from the publications DOS 42 00 954 and DOS 43 02 956. Benzimidazole derivatives having a PAF-antagonistic action are furthermore described in the publication U.S. Pat. No. 5, 314, 880.

The compounds according to the invention are partly covered by the scope of meaning of these publications.

It is known that increased blood levels of triglycerides (hypertriglyceridaemia) and cholesterol (hypercholesterolaemia) are associated with the origin of atherosclerotic changes to the vascular walls and coronary heart diseases.

A significantly increased risk of the development of coronary heart diseases furthermore exists if these two risk factors occur in combination, which in turn is accompanied by excessive production of apolipoprotein B-100. There is therefore still a great need to provide active medicaments for combating atherosclerosis and coronary heart diseases.

The present invention relates to indolyl-substituted phenylacetic acid derivatives of the general formula (I)

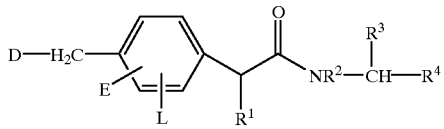

in which
D represents a radical of the formula

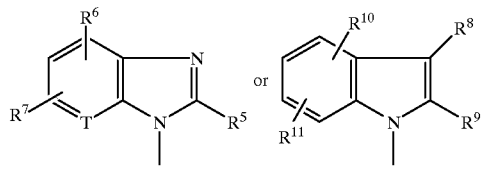

wherein
T denotes a nitrogen atom or the —CH group,
$R^6$, $R^7$, $R^{10}$ and $R^{11}$ are identical or different and denote hydrogen, trifluoromethyl, halogen or straight-chain or branched alkyl or alkoxy having in each case up to 6 carbon atoms,
$R^5$, $R^8$ and $R^9$ are identical or different and denote hydrogen, cycloalkyl having 3 to 6 carbon atoms, phenyl, straight-chain or branched alkoxycarbonyl having up to 6 carbon atoms or straight-chain or branched alkyl having up to 6 carbon atoms, which is optionally substituted by halogen,
or, in the case where T represents a nitrogen atom, $R^5$ can also denote benzyl,
E and L are identical or different and represent hydrogen, halogen, trifluoromethyl, hydroxyl or carboxyl, or represent straight-chain or branched alkyl, alkoxy or alkoxycarbonyl having in each case up to 6 carbon atoms, $R^1$ represents cycloalkyl having 3 to 10 carbon atoms, or represents straight-chain or branched alkyl having 1 to 10 carbon atoms, or represents phenyl, which is optionally substituted up to twice in an identical or different manner by halogen, cyano, hydroxyl or straight-chain or branched alkyl or alkoxy having in each case up to 4 carbon atoms,
$R^2$ represents hydrogen or straight-chain or branched alkyl having up to 3 carbon atoms,
$R^3$ represents hydrogen or straight-chain or branched alkyl having up to 5 carbon atoms, or represents cycloalkyl having 3 to 7 carbon atoms, or represents phenyl, or represents a 5- to 7-membered aromatic heterocyclic radical having up to 3 heteroatoms from the series consisting of S, N and/or O, each of which is optionally substituted up to 3 times in an identical or different manner by halogen, nitro, phenyl, hydroxyl or by straight-chain or branched alkyl or alkoxy having up to 6 carbon atoms,
$R^4$ represents hydrogen, or represents a group of the formula —$CH_2$—OH or $CHO_2O$—$R^{12}$,
wherein
$R^{12}$ denotes hydrogen, straight-chain or branched alkyl having up to 8 carbon atoms or phenyl, which is optionally substituted up to 3 times in an identical or different manner by halogen, hydroxyl, cyano or straight-chain or branched alkyl or alkoxy having in each case up to 4 carbon atoms, and salts thereof.

The phenylacetic acid derivatives with heterocyclic substituents and substituted imidazo[4,5-b] pyridines and benzimidazoles according to the invention can also be in the form of their salts. Salts with organic or inorganic bases or acids may be mentioned in general here.

Physiologically acceptable salts are preferred in the context of the present invention. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can likewise be metal or ammonium salts of the compounds according to the invention which have a free carboxyl group. Particularly preferred salts are, for example, sodium, potassium, magnesium or calcium salts, as well as ammonium salts which are derived from ammonia or organic amines, such as, for example, ethylarnine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as mirror images (enantiomers) or do not behave as mirror images (diastereomers). The invention relates both to the enantiomers or diastereomers and to the particular mixtures thereof. These mixtures of the enantiomers and diastereomers can be separated into the stereoisomerically uniform constituents in a known manner.

In the context of the invention, a heterocyclic radical, which is optionally benzo-fused, in general represents a saturated or unsaturated 5- to 7-membered, preferably 5- or 6-membered, heterocyclic radical which can contain up to 3 heteroatoms from the series consisting of S, N and/or O and which, in the case of a nitrogen atom, can also be bonded via this. Examples which may be mentioned are: indolyl, quinolyl, benzo[b]thienyl, benzo[b]furyl, pyridyl, thienyl, furyl, pyrrolyl, thiazolyl, oxazolyl, imidazolyl, morpholinyl or piperidyl. Quinolyl, firyl, pyridyl and thienyl are preferred.

Preferred compounds of the general formula (I) are those in which

D represents a radical of the formula

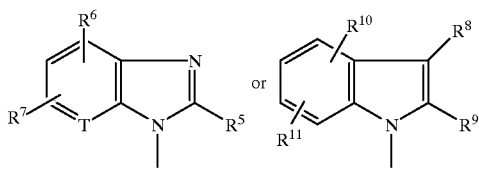

wherein

T denotes a nitrogen atom or the —CH group, $R^6$, $R^7$, $R^{10}$ and $R^{11}$ are identical or different and denote hydrogen, trifluoromethyl, fluorine, chlorine, bromine or straight-chain or branched alkyl or alkoxy having in each case up to 5 carbon atoms, $R^5$, $R^8$ and $R^9$ are identical or different and denote hydrogen, cyclopropyl, cyclopentyl, cyclohexyl,-phenyl, straight-chain or branched alkoxycarbonyl having up to 5 carbon atoms or straight-chain or branched alkyl having up to 5 carbon atoms, which is optionally substituted by fluorine, chlorine or bromine, or, in the case where T represents a nitrogen atom, $R^5$ can also denote benzyl, E and L are identical or different and represent hydrogen, fluorine, chlorine, bromine, trifluoromethyl, hydroxyl or straight-chain or branched alkyl or alkoxy having in each case up to 4 carbon atoms, $R^1$ represents cyclobutyl, cyclopentyl, cyclohexyl, cycloheptyl or cyclooctyl, or represents straight-chain or branched alkyl having up to 7 carbon atoms, or represents phenyl, which is optionally substituted by fluorine, chlorine, bromine, cyano, hydroxyl or straight-chain or branched alkyl or alkoxy having in each case up to 3 carbon atoms, $R^2$ denotes hydrogen or methyl, $R^3$ represents hydrogen or straight-chain or branched alkyl having up to 4 carbon atoms, cyclopropyl, cyclopentyl or cyclohexyl, or represents phenyl, pyridyl, thienyl or firyl, each of which is optionally substituted up to twice in an identical or different manner by fluorine, chlorine, bromine, phenyl, nitro, hydroxyl or by straight-chain or branched alkyl or alkoxy having up to 4 carbon atoms, $R^4$ represents hydrogen, or represents a group of the formula —$CH_2$—OH or —$CH_2O$—CO—$R^{12}$, wherein $R^{12}$ denotes hydrogen, straight-chain or branched alkyl having up to 6 carbon atoms or phenyl, which is optionally substituted up to twice in an identical or different manner by fluorine, chlorine, bromine, cyano, hydroxyl or straight-chain or branched alkyl or alkoxy having in each case up to 3 carbon atoms, and salts thereof.

Particularly preferred compounds of the general formula (I) are those
in which

D represents a radical of the formula

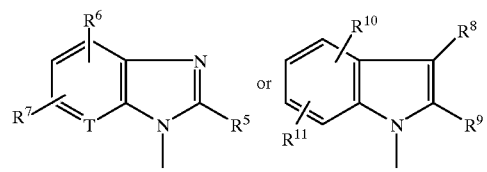

wherein

T denotes a nitrogen atom or the —CH group, $R^6$, $R^7$, $R^{10}$ and $R^{11}$ are identical or different and denote hydrogen, trifluoromethyl, chlorine or straight-chain or branched alkyl or alkoxy having in each case up to 4 carbon atoms, $R^5$, $R^8$ and $R^9$ are identical or different and denote hydrogen, cyclopropyl, cyclopentyl, cyclohexyl, phenyl, straight-chain or branched alkoxycarbonyl having up to 4 carbon atoms or straight-chain or b having up to 4 carbon atoms, which is optionally substituted by chlorine, or, in the case where T represents a nitrogen atom, $R^5$ can also denote benzyl, E and L are identical or different and represent hydrogen, fluorine, chlorine, bromine or trifluoromethyl, $R^1$ represents cyclopentyl, cyclohexyl, cycloheptyl or cyclooctyl, or represents straight-chain or branched alkyl having up to 6 carbon atoms, or represents phenyl, which is optionally substituted by fluorine, chlorine, cyano, hydroxyl, methyl or methoxy, $R^2$ represents hydrogen or methyl, $R^3$ represents hydrogen or straight-chain or branched alkyl having up to 3 carbon atoms, cyclopropyl, cyclopentyl or cyclohexyl, or represents pyridyl, thienyl or phenyl, each of which is optionally substituted up to twice in an identical or different manner by fluorine, chlorine, bromine, nitro, phenyl, hydroxyl or by straight-chain or branched alkyl or alkoxy having up to 3 carbon atoms, $R^4$ represents hydrogen, or represents a group of the formula —$CH_2$—OH or —$CH_2O$—CO—$R^{12}$, wherein $R^{12}$ denotes hydrogen, straight-chain or branched alkyl having up to 6 carbon atoms or phenyl, which is optionally substituted up to twice in an identical or different manner by fluorine, chlorine, bromine, cyano, hydroxyl, methyl or methoxy, and salts thereof.

A process has furthermore been found for the preparation of the compounds of the general formula (I) according to the invention, characterized in that compounds of the general formula (II)

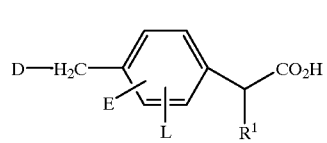

(II)

in which

D, E, L and $R^1$ have the abovementioned meaning, are reacted with compounds of the general formula (III)

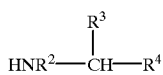

(III)

in which

R[2], [3] and R[4] have the abovementioned meaning, in inert solvents, if appropriate in the presence of a base and/or auxiliary.

The process according to the invention can be illustrated by the following equation by way of example:

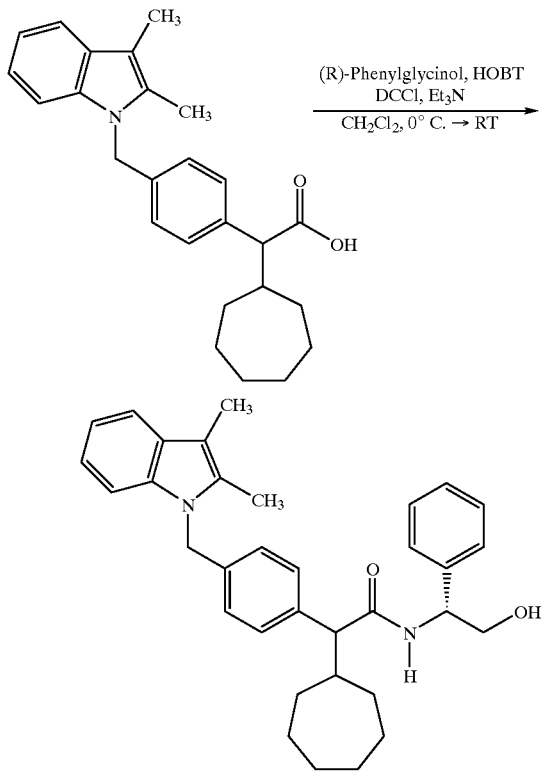

Suitable solvents for the process are customary organic solvents which do not change under the reaction conditions. These include, preferably, ethers, such as diethyl ether, dioxane, tetrahydrofliran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, triethylamine, pyridine, dimethyl sulphoxide, dimethylformamide, hexamethylphosphoric acid triamide, acetonitrile, acetone or nitromethane. It is also possible to use mixtures of the solvents mentioned. Methylene chloride; tetrahydrofuran and dimethylformamide are preferred.

Bases which can be employed for the process according to the invention are in general inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate, potassium carbonate or caesium carbonate, alkaline earth metal carbonates, such as calcium carbonate, or alkali metal or alkaline earth metal alcoholates, such as sodium or potassium methanolate, sodium or potassium ethanolate or potassium tert-butylate, or organic amines (trialkyl($C_1$–$C_6$)amines), such as triethylamine, or heterocyclic compounds, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium, or hydrides thereof, such as sodium hydride, as bases. Sodium hydride, potassium carbonate, triethylamine, trimethylamine, pyridine, potassium tert-butylate, DBU or DABCO are preferred.

The base is in general employed in an amount of 0.05 mol to 10 mol, preferably 1 mol to 2 mol, per mole of compound of the formula (II).

If appropriate, the amidation can proceed by the activated stage of the acid halides or mixed anhydrides, which can be prepared from the corresponding acids by reaction with thionyl chloride, phosphorus trichloride, phosphorus pentachloride, phosphorus tribromide or oxalyl chloride or methanesulphonyl chloride.

Suitable dehydrating reagents are carbodiimides, such as, for example, diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate, or propanephosphoric anhydride or isobutyl chloroformate or benzotriazolyloxy-tris-(dimethylamino)phosphonium hexafluorophosphate or phosphonic acid diphenyl esteramide or methanesulphonyl chloride, if appropriate in the presence of bases, such as triethylamine or N-ethylmorpholine or N-methylpiperidine or dicyclohexylcarbodiimide and N-hydroxysuccinimide.

The process according to the invention is in general carried out in a temperature range from –50° C. to +100° C., preferably from –30° C. to +60° C.

The process according to the invention is in general carried out under normal pressure. However, it is also possible to carry out the process under increased pressure or under reduced pressure (for example in a range from 0.5 to 5 bar).

The compounds of the general formula (II) are known in some cases or are novel, and can then be prepared, for example, by reaction of compounds of the general formula (IV)

D-H         (IV)

in which

D has the abovementioned meaning, with compounds of the general formula (V)

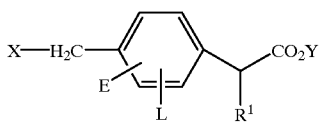

(V)

in which

E, L and R[1] have the abovementioned meaning,

X stands for halogen and

Y represents straight-chain or branched alkyl having up to 4 carbon atoms, in one of the abovementioned solvents and bases, and finally conversion of the esters into the corresponding acids by customary methods.

Dimethylformamide is preferably employed as the solvent.

Sodium hydride is preferably employed as the base.

The base is in general employed in an amount of 0.05 mol to 10 mol, preferably 1 mol to 2 mol, per mole of the compound of the formula (IV).

The process according to the invention is in general carried out in a temperature range from −50° C. to +100° C., preferably from −30° C to +60° C.

The process according to the invention is in general carried out under normal pressure. However, it is also possible to carry out the process under increased pressure or under reduced pressure (for example in a range from 0.5 to 5 bar).

The compounds of the general formula (III), (IV) and (V) are known per se or can be prepared by customary methods.

The compounds of the general formula (I) according to the invention have a pharmacological action spectrum which cannot be foreseen.

They can be used as active compounds in medicaments for reducing changes to vascular walls and for treatment of coronary heart diseases, cardiac insufficiency, disturbances in cerebral performance, ischaemic cerebral diseases, apoplexy, circulatory disturbances, disturbances in microcirculation and thromboses.

The proliferation of smooth muscle cells continues to play a decisive role in the occlusion of vessels. The compounds according to the invention are suitable for inhibiting this proliferation and therefore for preventing atherosclerotic processes.

The compounds according to the invention are distinguished by a reduction in ApoB-100-associated lipoproteins (VLDL and its breakdown products, such as, for example, LDL), ApoB-100, triglycerides and cholesterol. They therefore have valuable pharmacological properties which are superior to the prior art.

Surprisingly, the action of the compounds according to the invention initially comprises a reduction in or complete inhibition of the formation and/or release of ApoB-100-associated lipoproteins from hepatic cells, which results in a lowering of the plasma VLDL level. This lowering in VLDL must be accompanied by a lowering of the plasma level of ApoB-100, LDL, triglycerides and cholesterol; several of the abovementioned risk factors which participate in changes to the vascular wall are thus reduced simultaneously.

The compounds according to the invention can therefore be employed for prevention and treatment of atherosclerosis, obesity, pancreatitis and constipation.

1. Inhibition of the release of ApoB-100-associated lipoproteins

The test for detection of the inhibition of the release of ApoB-100-associated lipoproteins from hepatic cells was carried out in vitro with cultured hepatic cells, preferably with cells of the human line HepG2. These cells are cultured under standard conditions in medium for culture of eukaryotic cells, preferably in RPMI 1640 with 10% foetal calf serum. HepG2 cells synthesize and secrete into the culture supernatant ApoB-100-associated lipoprotein particles, which are in principle built up similarly to the VLDL and LDL particles which are to be found in plasma.

These particles can be detected with an immunoassay for human LDL. This immunoassay is carried out with antibodies which have been induced against human LDL in rabbits under standard conditions. The anti-LDL antibodies (rab-anti-LDL-Ab) were purified by affinity chromatography on an immunosorbent with human LDL.

These purified rab-anti-LDL-Ab are adsorbed onto the surface of plastic. This adsorption is expediently carried out on the plastic surface of microtiter plates with 96 wells, preferably on MaxiSorp plates. If ApoB-100-associated particles are present in the supenatant of Hep-G2 cells, these can then bond to the insolubilized rab-anti-LDL-Ab, and an immune complex bonded to the plastic surface is formed. Non-bonded proteins are removed by washing. The immune complex on the plastic surface is detected with monoclonal antibodies, which have been induced against human LDL and purified under standard conditions. These antibodies were conjugated with the enzyme peroxidase. Peroxidase converts the colourless substrate TMB into a coloured product in the presence of $H_2O_2$. After acidification of the reaction mixture with $H_2SO_4$, the specific adsorption of light is determined at 450 nm, this being a measure of the amount of ApoB-100-associated particles which had been secreted by the HepG2 cells into the culture supernatant.

Surprisingly, the compounds according to the invention inhibit the release of ApoB-100-associated particles. The $IC_{50}$ value indicates the concentration of substance at which the adsorption of light is inhibited by 50% compared with the control (solvent control without the substance).

| Example No. | $IC_{50}$ [$10^{-9}$ mol/l] |
|---|---|
| 2 | 29.5 |
| 3 | 62.5 |
| 4 | 40.5 |
| 5 | 83.2 |
| 6 | 37.4 |
| 7 | 228.9 |
| 8 | 50.5 |
| 11 | 489.2 |
| 12 | 10.8 |
| 13 | 24.6 |
| 14 | 473.5 |
| 15 | 47.3 |
| 16 | 35.9 |
| 17 | 38.1 |
| 20 | 8.1 |
| 21 | 4.5 |
| 22 | 23.5 |
| 23 | 36.1 |
| 26 | 26.8 |
| 27 | 6.5 |
| 28 | 62.6 |
| 29 | 40.5 |
| 30 | 128.5 |
| 31 | 428.3 |
| 32 | 48.5 |
| 33 | 41.1 |
| 34 | 12.3 |
| 35 | 308.0 |
| 36 | 72.5 |
| 37 | 31.1 |
| 38 | 269.7 |
| 39 | 29.4 |
| 40 | 93.6 |
| 41 | 40.4 |
| 42 | 9.3 |
| 43 | 5.0 |
| 44 | 130.6 |
| 45 | 302.4 |
| 46 | 58.9 |
| 47 | 78.6 |
| 48 | 491.2 |
| 49 | 78.6 |
| 50 | 420.6 |
| 51 | 78.6 |
| 52 | 58.9 |
| 53 | 491.2 |
| 54 | 56.7 |
| 55 | 18.9 |

-continued

| Example No. | IC$_{50}$ [10$^{-9}$ mol/l] |
|---|---|
| 56 | 170.1 |
| 57 | 10.8 |
| 58 | 1.5 |
| 59 | 26.9 |
| 60 | 9.5 |
| 62 | 151.9 |
| 63 | 1010.1 |
| 64 | 150.9 |
| 66 | 8.1 |
| 67 | 30.2 |
| 69 | 9.6 |

2. Determination of VLDL secretion in vivo on the hamster

The effect of the test substances on VLDL secretion in vivo is investigated on the hamster. For this, after premedication with atropine (83 mg/kg s.c.), golden hamsters are anaesthetized with Ketavet (83 mg/kg s.c.) and nembutal (50 mg/kg i.p.). When the animals had become reflex-free, the v. jugularis is exposed and cannulated. 0.25 ml/kg of a 20% strength solution of Triton WR-1339 in physiological saline solution is then administered. This detergent inhibits lipoprotein lipase and thus leads to an increase in the triglyceride level because of an absence of catabolism of secreted VLDL particles. This increase in triglycerides can be used as a measure for the rate of VLDL secretion. Blood was taken from the animals by puncture of the retroorbital venous plexus before and one and two hours after administration of the detergent. The blood is incubated at room temperature for two hours and then at 4° C. overnight in order to conclude coagulation completely. Thereafter, it is centrifuged at 10,000 g for 5 minutes. The triglyceride concentration in the serum thus obtained is determined with the aid of a modified commercially obtainable enzyme test (Merckotest® Triglyceride No. 14354). 100 μl of test reagent are added to 100 μl of serum in 96-well plates and the plates are incubated at room temperature for 10 minutes. The optical density is then determined at a wavelength of 492 nm in an automatic plate reader (SLT-Spectra). Serum samples having a triglyceride concentration which is too high are diluted with physiological saline solution. The triglyceride concentration contained in the samples is determined wish the aid of a standard curve measured in parallel. In this model, test substances are administered either intravenously immediately before administration of the detergent or orally or subcutaneously before initiation of the anaesthesia 3. Inhibition of intestinal triglycide absorbtion in vivo (rats)

The substances which are to be investigated in vivo for their inhibiting action on triglyceride absorption are administered orally to male Wistar rats having a body weight of between 170 and 230 g. For this purpose, the animals are divided into groups of 6 animals 18 hours before administration of the substance, and their food is then withdrawn. Drinking water is available to the animals ad libitum. The animals of the control groups are given an aqueous tragacanth suspension or a tragacanth suspension which comprises olive oil. The tragacanth-olive oil suspension is prepared with an Ultra-Turrax. The substances to be investigated are suspended in a corresponding tragacanth-olive oil suspension, likewise with an Ultra-Turrax, directly before administration of the substance.

Before administration by a stomach tube, blood is taken from each rat by puncture of the retroorbital venous plexus for determination of the basal serum triglyceride content.

The tragacanth suspension, the tragacanth-olive oil suspensions without a substance (control animals) or the substances, suspended in a corresponding tragacanth-olive oil suspension, are then administered to the fasting animals using a stomach tube. Further blood for determination of the postprandial serum triglyceride increase is as a rule taken 1, 2 and 3 hours after the administration by a stomach tube.

The blood samples are centrifuged and, after isolation of the serum, the triglycerides are determined photometrically with an EPOS-Analyzer 5060 (Eppendorf Geratebau, Netheler & Hinz GmbH, Hamburg). The triglycerides are determined completely enzymatically with a commercially available UV test.

The postprandial increase in serum triglycerides is determined by subtraction of the triglyceride prevalue of each animal from its corresponding postprandial triglyceride concentrations (1, 2 and 3 hours after administration).

The average is taken of the differences (in mmol/l) at each point in time (1, 2 and 3 hours) in the groups, and the means of the increase in serum triglycerides (ΔTG) of the animals treated with the substance are compared with the animals which received only the tragacanth-oil suspension.

The course of the serum triglycerides in the control animals, which were given only tragacanth, is also calculated. The effect of the substance at each point in time (1, 2 or 3 hours) is determined as follows and stated in Δ% of the oil-loaded control.

$$\Delta\% \text{ increase in triglyceride} = \frac{\Delta TG_{substance} - \Delta TG_{tragacanth\ control}}{\Delta TG_{oil\ loading} - \Delta TG_{tragacanth\ control}} \times 100$$

Effect of 10 mg of test substance/kg of body weight p.o. on the increase in triglycerides (Δ%) 2 hours after a triglyceride loading in the serum of fasting rats. The increase in serum triglycerides of fat-loaded control animals, based on the serum triglycerides level of tragacanth control animals, corresponds to 100%. n =6 animals per group.

The statistical analysis is carried out with the Student t-test after first checking the variances for homogeneity.

Substances which statistically significantly (p<0.05) reduce the postprandial increase in serum triglycerides by at least 30%, compared with the untreated control group, at a point in time are regarded as pharmacologically active.

| Example No. | TG absorption ED$_{50}$ or % inhibition mg/kg/p.o. |
|---|---|
| 2 | <3 mg/kg |
| 4 | <10 mg/kg |
| 12 | <<3 mg/kg |
| 13 | <3 mg/kg |
| 16 | >2 mg/kg |
| 20 | >>10 mg/kg |
| 21 | >>6 mg/kg |
| 23 | 2 mg/kg |
| 27 | >2 mg/kg |
| 29 | 3 mg/kg |
| 34 | 2 mg/kg |
| 37 | >2 mg/kg |
| 41 | 10 mg/kg |
| 42 | >2 mg/kg |
| 43 | 10 mg/kg |
| 46 | 30 mg/kg |
| 51 | 40 mg/kg |
| 54 | 50 mg/kg |
| 57 | >3 mg/kg |

| Example No. | TG absorption ED$_{50}$ or % inhibition mg/kg/p.o. |
|---|---|
| 60 | 10 mg/kg |
| 67 | >3 mg7kg |

4. Inhibition of VLDL secetion in vivo (rat)

The action of the test substances on VLDL secretion is also investigated on the rat. For this, Triton WR-1339, dissolved in physiological saline solution, is administered intravenously into the tail vein of rats of 500 mg/kg body weight (2.5 mg/kg). Triton WR-1339 inhibits lipoprotein lipase and thus leads to an increase in the triglyceride and cholesterol level due to inhibition of VLDL catabolism. These increases can be used as a measure of the rate of VLDL secretion.

Blood is taken from the animals by puncture of the retroorbital venous plexus before and one and two hours after administration of the detergent. The blood is incubated at room temperature for 1 hour, for coagulation, and the serum is isolated by centrifugation at 10,000 g for 20 seconds. The triglycerides are then determined photometrically at a wavelength of 540 nm by means of a commercially available coupled enzyme test (Sigma Diagnostics®, No. 339). Measurement is carried out with the aid of a similarly coupled enzyme test (Boehringer Mannheim®, No. 1442350) at a wavelength of 546 nm. Samples with triglyceride or cholesterol concentrations which exceed the measurement range of the methods are diluted with physiological saline solution. The particular serum concentrations are determined with the aid of standard series measured in parallel. Test substances are administered orally, intravenously or subcutaneously immediately after the Triton injection.

The invention furthermore relates to the combination of phenylacetic acid derivatives with heterocyclic substituents and substituted imidazo[4.5-b]pyridines and benzimidazoles of the general formula (I) with a glucosidase and/or amylase inhibitor for treatment of familial hyperlipidaemias, obesity (adiposity) and diabetes mellitus.

Glucosidase and/or amylase inhibitors in the context of the invention are, for example, acaibose, adiposine, voglibose (AO-128), miglitol, emiglitate, MDL-25637, camiglibase (MDL-73945), temdamistate, AI-3688, trestatin, pradimicin-Q and salbostatin. The combination of acarbose, miglitol, emiglitate or vaglibose with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should be present here in each case in a concentration of about 0.5 to 90% by weight of the total mixture, i.e. in amounts which are sufficient to achieve the stated dosage range.

The formulations are prepared, for example, by extending the active compounds with solvents and/or excipients, if appropriate using emulsifying agents and/or dispersing agents, it being possible, for example in the case where water is used as the diluent, to use organic solvents as auxiliary solvents if appropriate.

The formulations are administered in the customary manner, preferably orally or parenterally, in particular perlingually or intravenously.

In the case of parenteral use, solutions of the active compound can be employed, using suitable liquid carrier materials.

In general, it has proved advantageous in the case of intravenous administration to administer amounts of about 0.001 to 1 mg/kg, preferably about 0.01 to 0.5 mg/kg of body weight to achieve effective results, and in the case of oral administration the dosage is about 0.01 to 20 mg/kg, preferably 0.1 to 10 mg/kg of body weight.

Nevertheless, it may be necessary, if appropriate, to deviate from the amounts mentioned, in particular as a function of the body weight or the nature of the administration route, of the behaviour of the individual towards the medicament, the nature of the formulation thereof and the time or interval at which administration takes place. Thus, in some cases it may be sufficient to manage with less than the abovementioned minimum amount, while in other cases the upper limit mentioned must be exceeded. In the case where relatively large amounts are administered, it may be advisable to divide these into several individual doses over the course of the day.

Abbreviations Used
bs=Broad singlet
CI=Chemical Ionization
cHept=Cycloheptyl
cHex=Cyclohexyl
cPent=Cyclopentyl
DCCI=N'-(3-Dimethylaminopropyl)-N'-ethylcarbodiimide
d=Doublet
dia=Diastereomer
dd=Doublet doublets
DMF=N,N-Dimethylformamide
DMSO=Dimethyl sulphoxide
EI=Electron impact ionization
FAB=Fast Atom Bombardment
HOBT=1-Hydroxy-1H-benzotriazole
Hz=Hertz
iBu=Isobutyl
iPr=Isopropyl
m=Multiplet
Me=Methyl
nPr=Normal propyl
Ph=Phenyl
RT=Room temperature
s=Singlet
t=Triplet
TFA=Trifluoroacetic acid
THF=Tetrahydrofuran
TMS=Tetramethylsilane
Solvent Mixtures Used
Petroleum ether:acetone=1:1 (A)
Petroleum ether:ethyl acetate=20:1 (B)
Petroleum ether:ethyl acetate=10:1 (C)
Petroleum ether:ethyl acetate=5:1 (D)
Petroleum ether:ethyl acetate 3:1 (E)
Petroleum ether:ethyl acetate=4:1 (F)
Petroleum ether:ethyl acetate=2:1 (G)
Petroleum ether:ethyl acetate=1:1 (H)
Petroleum ether:ethyl acetate=1:2 (I)
Methylene chloride:methanol=50:1 (J)
Methylene chloride:methanol=20:1 (K)
Methylene chloride:methanol=10:1 (L)
Methylene chloride:ethyl acetate=1:1 (M)
Methylene chloride:ethanol=50:1 (N)
Methylene chloride (100%)=(O)
Ethyl acetate:methanol=10:1 (P)
Toluene (100%)=(Q)

Toluene:ethyl acetate=1:1 (R)
Toluene:ethyl acetate=8:1 (S)
Toluene:ethyl acetate=9:1 (T)
Cyclohexanol:ethyl acetate=1:1 (U)
Cyclohexanol:ethyl acetate=7:3 (V)
Additional Information
If FAB has not been used, the following identifications apply in all the Tables which follow:
*=EI
=CI ($NH_3$)

EXAMPLE I

Methyl 2-(R&S)-phenyl-2-(4-methyl)phenylacetate

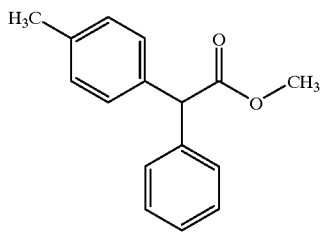

21.0 g (100 mmol, apin) of 2-phenyl-1-(4-methyl)phenyl-1-oxoethane and 38.8 g (120 mmol) of iodobenzene diacetate were dissolved in 300 ml of trimethyl orthoformate. 19.6 g of concentrated sulphuric acid were added to this solution and the solution was heated at 60° C. for 6 hours. It was cooled to room temperature, diluted with water (100 ml) and extracted with diethyl ether. The combined organic phases were dried over sodium sulphate and concentrated on a rotary evaporator. The residue was purified by column chromatography.

Yield 13.1 g (55%);

$R_f$=0.33 (petroleum ether:ethyl acetate=20:1);

Mass (calculated) for $C_{16}H_{16}O_2$=240.30; mass spectrum (FAB, relative intensity) 241 (25%), 181 (100%);

$^1$H NMR (200 MHz, $CDCl_3$)δ7.3–7.10 (m,9H), 4.99 (s, 1 H), 3.73 (s, 3 H), 2.31 (s, 3 H).

EXAMPLE II tert-Butyl 2-cyclopentyl-2-(4-methylphenyl)-acetate

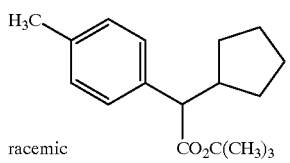

33.5 g (0.3 mol) of potassium tert-butylate are initially introduced into 100 ml of anhydrous DMF at 0° C., and 51.6 g (0.25 mol) of tert-butyl 4-methylphenyl-acetate in 250 ml of anhydrous DMF are added dropwise. The mixture is stirred at 0° C. for 30 minutes, 32.2 ml (0.3 mol) of cyclopentyl bromide in 150 ml of anhydrous DMF are added dropwise at 5–15° C. and the mixture is stirred at 25° C. for 20 hours. After concentration, the residue is partitioned between water and diethyl ether and the ether phase is dried over sodium sulphate and concentrated. The product crystallizes out.

Yield: 67 g (97.5% of theory);

Melting point: 51–53° C.

The compounds of Table I are prepared analogously to the instructions of Example II:

TABLE I

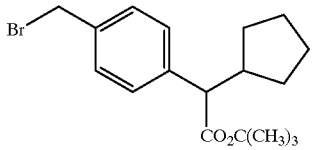

| Example No. | $R^1$ | $R^{18}$ | $R_f$* |
|---|---|---|---|
| III | (R&S) iPr | Me | 0.86 (T) |
| IV | (R&S) iBu | tBu | 0.84 (S) |
| V | (R&S) cPent | Me | 0.59 (C) |
| VI | (R&S) cHex | Me | 0.38 (B) |
| VII | (R&S) cHex | tBu | 0.71 (Q) |
| VIII | (R&S) cHept | Me | 0.57 (Q) |
| IX | (R&S) cHept | tBu | 0.32 (Q) |

EXAMPLE X tert-Butyl 2-(4-bromomethyl-phenyl)-2-cyclopentyl-acetate 27.4 g (0.1 mol) of the compound from Example II are dissolved in 200 ml of carbon tetrachloride and the solution is heated to the boiling point After addition of 0.82 g of azobisisobutyronitrile, 18.7 g (0.105 mol) of N-bromosuccinimide are added in portions, the mixture is then refluxed for 1 hour and cooled to 0° C. and the succinimide is filtered off. After concentration of the filtrate, the product precipitates out. It is washed with petroleum ether (40/60) and dried.

Yield: 20 g (57% of theory);

Melting point: 73–76° C.

The compounds of Table II are prepared analogously to the instructions of Example X:

TABLE II

| Example No. | $R^1$ | $R^{13}$ | $R_f$* |
|---|---|---|---|
| XI | (R&S) iPr | Me | 0.78 (O) |
| XII | (R&S) iBu | tBu | 0.86 (O) |

TABLE II-continued

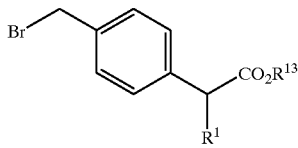

| Example No. | R¹ | R¹³ | $R_f$* |
|---|---|---|---|
| XIII | (R&S) cPent | Me | 0.63 (C) |
| XIV | (R&S) cHex | Me | 0.74 (O) |
| XV | (R&S) cHex | tBu | 0.58 (C) |
| XVI | (R&S) cHept | tBu | 0.84 (O) |
| XVII | (R&S) Ph | Me | 0.74 (O) |

EXAMPLE XVIII
4-Methyl-2-propyl-1H-benzimidazole

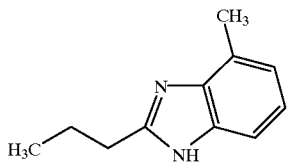

5.00 g (41 mmol) of 2,3-diamino-toluene and 3.7 ml (41 mmol) of butyric acid are stirred in 41 ml of polyphosphoric acid at 120° C. for 3 hours, and the mixture is poured into 410 ml of water and brought to pH=9 with solid sodium hydride. Thereafter, sodium carbonate is added until the evolution of carbon dioxide has ended, the mixture is extracted five times with 100 ml of ethyl acetate each time, the combined organic phases are dried with anhydrous sodium sulphate and the solution is evaporated - finally under a high vacuum; crude weight: 5.89 g.

The product is purified by chromatography over silica gel 60 (Merck/40–63 μm/methylene chloride:methanol=100:1); yield: 2.45 (34%). $R_f$=0.16 (methylene chloride:methanol= 20:1)

The compounds listed in Table III are prepared analogously to the instructions of Example XVIII:

| Example No. | D | Yield (% of theory) | $R_f$ (solvent) | Melting point (° C.) | MS (EI) (relative intensity) |
|---|---|---|---|---|---|
| XIX | benzimidazole-cHex | 97 | 0.85 (P) | >240 | 200 (30%), 145 (100%) |
| XX | imidazo[4,5-b]pyridine-Ph | 81 | 0.66 (P) | >220 | 199 (100%) |
| XXI | Me,Me-imidazo-Bn | 27 | 0.39 (K) | 184 | 238 (100%) |
| XXII | Me,Me-imidazo-Ph | 23 | 0.39 (K) | 240 | #224 (100%) |

EXAMPLE XXIII tert-Butyl 2-cycloheptyl-2-[4-(2,3-dimethylindol-1-ylmethyl)phenyl]acetate

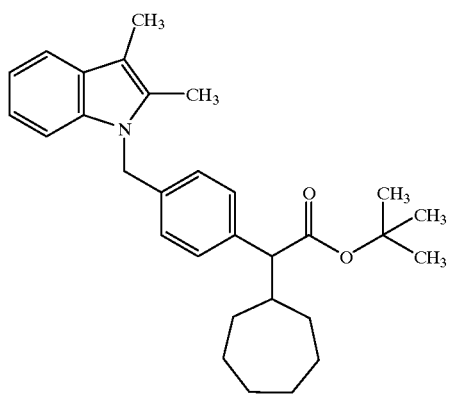

1.0 g (6.2 mmol) of 2,3-dimethylindole is dissolved in 10 ml of DMF. The solution is cooled to 0° C. under argon. 0.32 g (8.0 mmol) of sodium hydride (60% pure in paraffin) is added in portions. The mixture is subsequently stirred at 0° C,. for half an hour. A solution of 3.5 g (6.2 mmol) of XVI in 40 ml of DMF is slowly added dropwise. The mixture is subsequently stirred at room temperature overnight. The DMF is distilled off using a high vacuum and the residue is partitioned in water and ethyl acetate. The organic phase is dried over sodium sulphate and concentrated on a rotary evaporator. The residue is purified by column chromatography (silica gel Merck 60 (0.040-0.063)):

Yield: 1.3 g (42.3%);

Melting point=121–123° C.;

$R_f$=0.42 (petroleum ether:ethyl acetate=20:1);

Mass (calculated) for $C_{30}H_{39}NO_2$=445.65: mass spectrum (DCI ($NH_3$), relative intensity) 445 (100%), 389 (30%);

$^1$H NMR (250 MHz, $CDCl_3$)δ7.52 (m, 1 H), 7.22–7.18 (m, 3 H), 7.15–7.05 (m, 2 6.89 (d, J=8.22 Hz, 2 H), 5.25 (s, 2 H ), 3.12 (d, J=10.83 Hz, 1 H), 2.28 (s, 3 H), 2.27 (s, 3 H), 2.12 (ma, 1 H), 1.84–1.20 (m, 11 H), 1.36 (s, 9 H), 0.90 (m,1 H).

The compounds listed in Table IV are prepared analogously to the instructions of Example XXIII:

TABLE IV

| Example No. | D | $R^{14}$ | $R^1$ | Yield (% of theory) | Rf (solvent) | Melting point (° C.) | MS(*) (relative intensity) |
|---|---|---|---|---|---|---|---|
| XXIV | indole | tBu | (R&S) cHept | 48 | 0.43 (B) | 123–124 | #418 (100%) |
| XXV | 2-methylindole | tBu | (R&S) cHept | 49 | 0.43 (B) | 124–26 | *431 (100%), 57 (70%) |
| XXVI | 2,3-dimethylindole | tBu | (R&S) cPent | 24 | 0.25 (B) | 115 | 417 (100%), 360 (20%) |
| XXVI | 2,3-dimethylindole | Me | (R&S) cHex | 55 | 0.35 (K) | 98–101 | 389 (100%) |

TABLE IV-continued

[Structure: 4-(D-CH2)-phenyl-CH(R1)-C(=O)-OR14]

| Example No. | D | R14 | R1 | Yield (% of theory) | Rf (solvent) | Melting point (° C.) | MS(*) (relative intensity) |
|---|---|---|---|---|---|---|---|
| XXVIII | 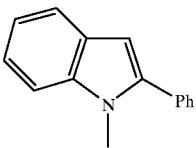 1-Ph, N-Me indole | tBu | (R&S) cHept | 39 | 0.39 (B) | | *493 (20%), 57 (100%) |
| XXIX | 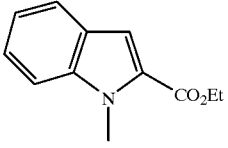 N-Me, 2-CO2Et indole | tBu | (R&S) cPent | 48 | 0.46 (C) | 86 | 461 (85%), 406 (100%) |
| XXX | 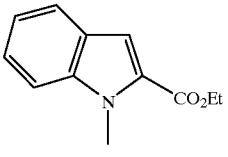 N-Me, 2-CO2Et indole | tBu | (R&S) cHept | 43 | 0.32 (B) | | *489 (60%), 57 (100%) |
| XXXI | 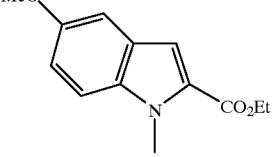 5-MeO, N-Me, 2-CO2Et indole | tBu | (R&S) cPent | 42 | 0.58 (O) | 106 | 491 (100%), 436 (40%), 57 (60%) |
| XXXII | 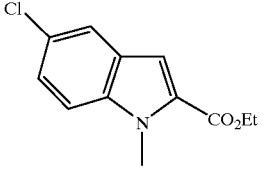 5-Cl, N-Me, 2-CO2Et indole | tBu | (R&S) cPent | 64 | 0.25 (L) | 100–02 | 495 (70%), 440 (100%), 57 (100%) |
| XXXIII | 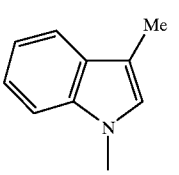 3-Me, N-Me indole | tBu | (R&S) cHept | 76 | 0.41 (B) | 100–01 | #431 (20%), 375 (100%) |
| XXXIV | 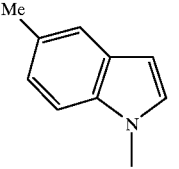 5-Me, N-Me indole | tBu | (R&S) cPent | 65 | 0.42 (B) | | 403 (20%), 346 (40%) |

TABLE IV-continued

[Structure: 4-(D-CH2)-phenyl-CH(R1)-C(=O)-OR14]

| Example No. | D | R14 | R1 | Yield (% of theory) | Rf (solvent) | Melting point (° C.) | MS(*) (relative intensity) |
|---|---|---|---|---|---|---|---|
| XXXV | 7-Me-1-methylindol-3-yl | tBu | (R&S) cPent | 67 | 0.33 (B) | | #404 (100%) |
| XXXVI | 5-Cl-1-methylindol-3-yl | tBu | (R&S) cHept | 54 | 0.35 (B) | | *451 (30%), 57 (100%) |
| XXXVII | 6-Cl-1-methylindol-3-yl | tBu | (R&S) cPent | 75 | 0.34 (B) | | 423 (100%) |
| XXXVIII | 4-OMe-1-methylindol-3-yl | tBu | (R&S) cPent | 79 | 0.25 (B) | | #420 (100%) |
| XXXIX | 5-OMe-1-methylindol-3-yl | tBu | (R&S) cHept | 53 | 0.24 (B) | | *447 (100%), 57 (60%) |
| XL | 1-methylbenzimidazol-2-yl | tBu | (R&S) cHept | 67 | 0.14 (J) | | *418 (10%), 57 (100%) |
| XLI | 1,2-dimethylbenzimidazol-2-yl | tBu | (R&S) cHept | 96 | 0.42 (K) | 109 | *432 (100%) |

TABLE IV-continued

[Structure: 4-(CH₂-D)-C₆H₄-CH(R¹)-C(=O)-OR¹⁴]

| Example No. | D | R¹⁴ | R¹ | Yield (% of theory) | Rf (solvent) | Melting point (° C.) | MS(*) (relative intensity) |
|---|---|---|---|---|---|---|---|
| XLII | 4,6-dichloro-1,2-dimethyl-benzimidazol-2-yl (Cl, Cl, Me, N-Me) | tBu | (R&S) cPent | 53 | 0.20 (E) | | 475 (80%), 473 (100%) |
| XLIII | 2-iPr-1-Me-benzimidazol-... | tBu | (R&S) cPent | 70 | 0.48 (J) | 111 | |
| XLIV | 2-nBu-1-Me-benzimidazol-... | tBu | (R&S) cPent | 94 | 0.81 (K) | | |
| XLV | 2-tBu-1-Me-benzimidazol-... | tBu | (R&S) cPent | 55 | 0.64 (J) | 134 | 447 (100%) |
| XLVI | 2-cHex-1-Me-benzimidazol-... | tBu | (R&S) cPent | 66 | 0.47 (K) | 56 | 473 (100%), 57 (40%) |
| XLVII | 4-Me-2-nPr-1-Me-benzimidazol-... | tBu | (R&S) cPent | 80 | 0.51 (G) | | |
| XLVIII | 2-Ph-1-Me-benzimidazol-... | tBu | (R&S) cPent | 61 | 0.27 (H) | | |
| XLIX | 2-Ph-1-Me-benzimidazol-... | tBu | (R&S) cHept | 20 | 0.28 (V) | 0:1 | |

TABLE IV-continued

[Structure: 4-substituted benzyl group with -CH(R¹)-C(=O)-OR¹⁴, where D = CH₂ substituent on para position]

| Example No. | D | R¹⁴ | R¹ | Yield (% of theory) | Rf (solvent) | Melting point (° C.) | MS(*) (relative intensity) |
|---|---|---|---|---|---|---|---|
| L | 2-cyclopropyl-3-methyl-imidazo[4,5-b]pyridinyl | tBu | (R&S) cPent | 27 | 0.64 (K) | | 432 (40%), 57 (100%) |
| LI | 2-phenyl-3-methyl-imidazo[4,5-b]pyridinyl | tBu | (R&S) cPent | 97 | 0.47 (L) | 0:1 | |
| LII | 2,3,5,7-tetramethyl-imidazo[4,5-b]pyridinyl | tBu | (R&S) cPent | 32 | 0.29 (J) | 92 | 434 (100%), 162 (65%) |
| LIII | 2,3,5,7-tetramethyl-imidazo[4,5-b]pyridinyl | Me | (R&S) cHex | 29 | 0.59 (K) | 0:1 | 406 (100%) |
| LIV | 2-cyclopropyl-3,5,7-trimethyl-imidazo[4,5-b]pyridinyl | tBu | (R&S) cPent | 43 | 0.14 (J) | 118 | 460 (100%), 188 (20%) |
| LV | 2-benzyl-3,5,7-trimethyl-imidazo[4,5-b]pyridinyl | tBu | (R&S) cPent | 60 | 0.36 (J) | 110 | 510 (100%), 57 (25%) |
| LVI | 2-phenyl-3,5,7-trimethyl-imidazo[4,5-b]pyridinyl | tBu | (R&S) cPent | 56 | 0.55 (J) 0.83 (K) | | #496 (100%) |

EXAMPLES LVII AND LVIII 2.30 g (5.0 mmol) of the compound from Example LIV are dissolved in 30 ml of dioxane, and 2.3 ml of concentrated hydrochloric acid are added to the solution. The mixture is boiled to reflux overnight and cooled, and 30 ml of cold water are added. The precipitate formed is filtered off with suction and dried:

Yield: 1.68 g

Since, according to NMR and mass, two compounds have been formed, these were separated by HPLC.

Cyclopentyl-[4-(2-cyclopropyl-5,7-dimethylimidazo[4,5-b]pyridin-3-yl)-phenyl]-acetic acid

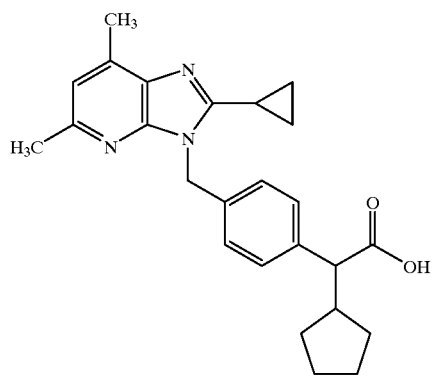

(LVII)

Melting point=180° C.;
Rf=0.24 ($CH_2Cl_2$:methanol=100:5);
Mass (calculated) for $C_{25}H_{29}N_3O_2$=403.53: mass spectrum (FAB, relative intensity) 404 (100%).

{4-[2-(3-Chloropropyl)-5,7-dimethylimidazo[4,5-b]pyridin-3-yl]-phenyl}-cyclopentylacetic acid

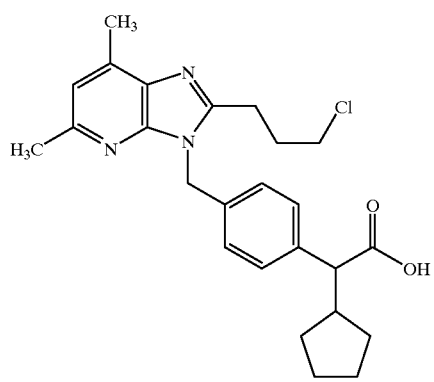

(LVIII)

Melting point=214° C.;
Rf=0.24 ($CH_2Cl_2$:methanol=100:5);

Mass (calculated) for $C_{25}H_{30}ClN_3O_2$=439.99: mass spectrum (FAB, relative intensity) 440 (75%).

EXAMPLE LIX

2-Cycloheptyl-2-[4-(2,3-dimethylindol-1-ylmethyl)phenyl]acetic acid

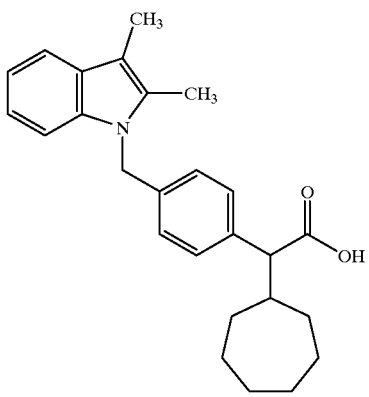

1.3 g (2.92 mmol) of the compound from Example XXII are dissolved in 15 ml of dioxane. 1.6 ml of concentrated hydrochloric acid are added and the mixture is boiled to reflux for 6 hours. Water and $CH_2C_2$, are added and the mixture is extracted. The organic phase is dried over sodium sulphate and concentrated on a rotary evaporator. The residue is purified by column chromatography (silica gel Merck 60 (0.040-0.063)):

Yield: 1.0 g (88.0%);

$R_f$=0.25 (petroleum ether:ethyl acetate=3:1);

Mass (calculated) for $C_{26}H_{31}NO_2$=389.54; mass spectrum (EI, relative intensity) 389 (100%), 149 (45%);

$^1$H NMR (200 MHz, $CDCl_3$) δ7.51 (m,1H), 7.22–7.05 (m, 5 H), 6.89 (d, J=8.11 Hz, 2 H), 5.25 (s, 2 H), 3.20 (d, J=10.88 Hz, 1 H), 2.27 (s, 6 H), 2.18 (m, 1 H), 1.80 (m, 1 H), 1.70–1.17 (m, 10 H), 0.95 (m, 1 H).

TABLE V
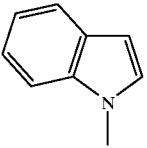
| Example No. | D | R¹ | Yield (% of theory) | R_f (solvent) | Melting point (° C.) | MS(*) (relative intensity) |
|---|---|---|---|---|---|---|
| LX | 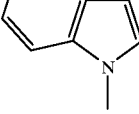 | (R&S) cHept | 72 | 0.52 (R) | | #362 (100%) |
| LXI | 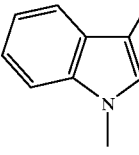 | (R&S) cHept | 77 | 0.53 (R) | | #376 (100%) |
| LXII | 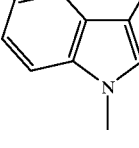 | (R&S) cPent | 80 | 0.26 (E) | 173 | 361 (100%) |
| LXIII | 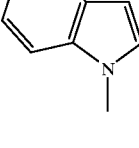 | (R&S) cHex | 87 | 0.51 (K) | 209 | 375 (100%) |
| LXIV | 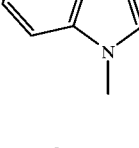 | (R&S) cHept | 49 | 0.28 (K) | | *437 (100%), 55 (100%) |
| LXV | 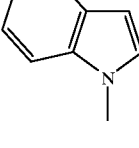 | (R&S) cPent | 72 | 0.47 (K) | 186 | 406 (80%), 405 (100%) |
| LXVI |  | (R&S) cHept | 68 | 0.29 (K) | | *433 (100%) |

TABLE V-continued
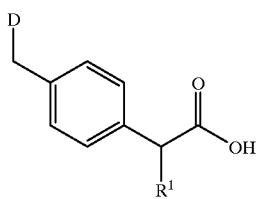
| Example No. | D | R¹ | Yield (% of theory) | R_f (solvent) | Melting point (° C.) | MS(*) (relative intensity) |
|---|---|---|---|---|---|---|
| LXVII | 5-MeO, 1-Me, 2-CO₂Et indole | (R&S) cPent | 79 | 0.48 (K) | 142 | 435 (100%) |
| LXVIII | 5-Cl, 1-Me, 2-CO₂Et indole | (R&S) cPent | 94 | 0.48 (K) | 67 (Foam) | 439 (100%), 217 (80%) |
| LXIX | 3-Me, 1-Me indole | (R&S) cHept | 78 | 0.27 (E) | | *395 (100%) |
| LXX | 5-Me, 1-Me indole | (R&S) cPent | 64 | 0.44 (K) | oil | *347 (80%), 88 (100%) |
| LXXI | 7-Me, 1-Me indole | (R&S) cPent | 68 | 0.62 (K) | | *347 (60%), 149 (100%) |
| LXXII | 5-Cl, 1-Me indole | (R&S) cHept | 70 | 0.33 (K) | | *395 (80%), 149 (100%) |
| LXXIII | 6-Cl, 1-Me indole | (R&S) cPent | 88 | 0.51 (K) | oil | *367 (100%) |

TABLE V-continued

Structure: 4-(D-CH2)-phenyl-CH(R1)-COOH

| Example No. | D | R1 | Yield (% of theory) | Rf (solvent) | Melting point (° C.) | MS(*) (relative intensity) |
|---|---|---|---|---|---|---|
| LXXIV | 4-OMe-1-methylindol-?-yl | (R&S) cPent | 92 | 0.44 (K) | | *363 (100%) |
| LXXV | 5-MeO-1-methylindol-?-yl | (R&S) cHept | 63 | 0.37 (K) | | *391 (100%) |
| LXXVI | 1-methylbenzimidazol-2-yl | (R&S) cHept | 68 | 0.18 (K) 0.50 (L) | 123 (Foam) | #363 (100%), 362 (90%) |
| LXXVII | 1,2-dimethylbenzimidazol-?-yl | (R&S) cHept | 100 | 0.16 (K) | 108 | *376 (100%) |
| LXXVIII | 4,6-dichloro-1,2-dimethylbenzimidazol-?-yl | (R&S) cPent | 100 | 0.07 (K) | >220 | 419 (60%), 417 (100%) |
| LXXIX | 2-iPr-1-methylbenzimidazol-?-yl | (R&S) cPent | 80 | 0.32 (K) | 234 | 377 (100%) |
| LXXX | 2-nBu-1-methylbenzimidazol-?-yl | (R&S) cPent | 92 | 0.44 (K) | | |

TABLE V-continued

| Example No. | D | R¹ | Yield (% of theory) | R_f (solvent) | Melting point (° C.) | MS(*) (relative intensity) |
|---|---|---|---|---|---|---|
| LXXXI | benzimidazole, 1-Me, 2-tBu | (R&S) cPent | 88 | 0.27 (K) | 126 (Foam) | 391 (100%) |
| LXXXII | benzimidazole, 1-Me, 2-cHex | (R&S) cPent | 99 | 0.44 (L) | 92 (Foam) | 417 (100%) |
| LXXXIII | benzimidazole, 4-Me, 1-Me, 2-nPr | (R&S) cPent | 89 | 0.10 (K) | | |
| LXXXIV | benzimidazole, 1-Me, 2-Ph | (R&S) cPent | 81 | 0.30 (L) | | |
| LXXXV | benzimidazole, 1-Me, 2-Ph | (R&S) cHept | 97 | 0.57 (L) | 113 (Foam) | *438 (100%) |
| LXXXVI | imidazo[4,5-b]pyridine, 1-Me, 2-cyclopropyl | (R&S) cPent | 71 | 0.25 (K) | | 376 (100%), 160 (40%) |
| LXXXVII | imidazo[4,5-b]pyridine, 1-Me, 2-Ph | (R&S) cPent | 46 | 0.07 (L) | | |
| LXXXVIII | imidazo[4,5-b]pyridine, 4,6-diMe, 1-Me, 2-Me | (R&S) cPent | 96 | 0.24 (K) | >230 | 378 (100%), 154 (60%) |

TABLE V-continued

[Structure: 4-(D-methyl)phenyl group attached to CH(R¹)-COOH]

| Example No. | D | R¹ | Yield (% of theory) | R_f (solvent) | Melting point (° C.) | MS(*) (relative intensity) |
|---|---|---|---|---|---|---|
| LXXXIX | 2,5,7-trimethyl-imidazo[4,5-b]pyridine (Me, Me, Me) | (R&S) cHex | 71 | 0.27 (K) | 120 (Foam) | 392 (100%) |
| XC | 2-Bn-5,7-dimethyl-imidazo[4,5-b]pyridine | (R&S) cPent | 87 | 0.16 (K) | 205 | #454 (100%) |
| XCI | 2-Ph-5,7-dimethyl-imidazo[4,5-b]pyridine | (R&S) cPent | 37 | 0.37 (K) | 160 | 440 (100%) |

TABLE VI

[Structure: 4-(D-methyl)phenyl group attached to CH(R¹)-CO₂-R¹⁵]

| Example No. | D | R¹ | R¹⁵ | Melting point (° C.) | Yield (% of theory) | R_f (solvent) | MS (relative intensity) |
|---|---|---|---|---|---|---|---|
| XCII | 4,6-bis(CF₃)-2-CH₃-benzimidazole | (R&S) cPent | tBu | — | 30 | 0.37 (E) | 541 (100%) 57 (60%) |
| XCIII | 4,6-bis(CF₃)-2-CH₃-benzimidazole | (R&S) cPent | H | >220 | 84 | 0.09 (K) | 485 (100%) |

Preparation Examples

Example 1

2-(R)- and 2-(S)-2-[4-(2-phenyl-1 H-benzimidazol-1-ylmethyl)-phenyl]-2-cyclopentyl-acetic acid (2-(R)-2-phenyl-glycinol)-amide

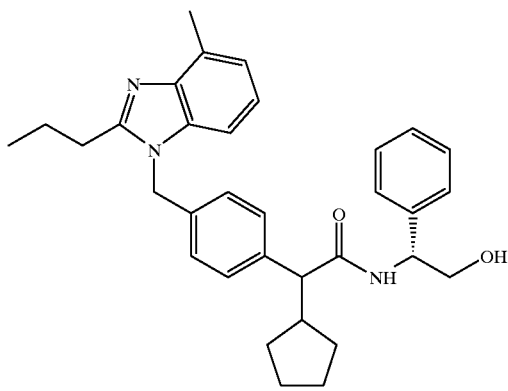

500 mg (1.22 mmol) of the compound from Example LXXXIII and 0.68 ml of triethylamine are reacted with 0.10 ml of mesyl chloride in 15 ml of anhydrous N,N-dimethylformamide at -30° C. for 30 minutes. Thereafter, a solution of 201 mg (1.46 mmol) of 2-(R)-2-phenyl-glycinol and 149 mg (1.22 mmol) of 4-N,N-dimethylamino)-pyridine in 15 ml of anhydrous N,N-dimethylformamide is added at -30° C. and the mixture is subsequently stirred at the stated temperature for one hour. After a total stirring time of 20 hours, with gradual warming to about 20° C., the mixture is poured onto ethyl acetate and aqueous sodium bicarbonate solution, the phases are separated and the aqueous solution is rinsed twice with ethyl acetate. The combined organic phases are then extracted in succession with water (2 ×), 1 M sodium hydroxide solution (3 ×), water (1 ×) and buffer of pH=2 (2 ×), dried with anhydrous sodium sulphate and evaporated - finally under a high vacuum.

Yield: 640 mg (1.2 mmol/99%);

$R_f$ 0.46 (methylene chloride:methanol=10:1).

Example 2

2-Cycloheptyl-N-(2-hydroxy-1-(R)-phenylethyl)-2-[4-(2,3-dimethylindol-1-yl-methyl) phenyl] acetamide

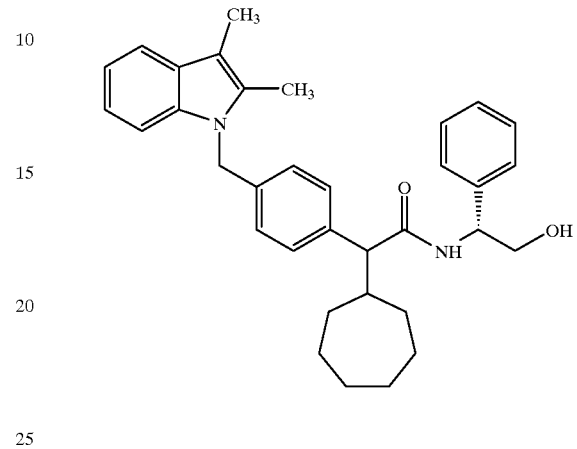

538 mg (1.38 mmol) of the compound from Example LIX are dissolved in 10 ml of $CH_2Cl_2$. 265 mg (1.38 mmol) of R-phenylglycinol are added. The solution is cooled to 0° C. and 204 mg (1.51 mmol) of 1-hydroxy-1-benzotriazole and 304 mg (1.58 mmol) of N'-(3-dimethylaminopropyl)-N-ethylcarbodiimide x HCl are subsequently added. 279 mg (2.76 mmol) of triethylamine are added dropwise. The mixture is subsequently stirred overnight at room temperature. Water and $CH_2Cl_2$ are added and the mixture is subjected to extraction. The organic phase is dried over sodium sulphate and concentrated on a rotary evaporator. The residue is purified by column chromatography (silica gel Merck 60 (0.004–0.063)).

Yield: 600 mg (85.4%);

Melting point: 163° C.;

$R_f$=0.77 ($CH_2Cl_2$:methanol=10:1);

Mass calculated for $C34N_{40}N_2O_2$=508.71; mass spectrum (DCI ($NH_3$), relative intensity) 509 (50%), 508 (100%).

The compounds listed in Table 1 are prepared analogously to the instructions of Examples 1 and 2:

TABLE 1

[Structure: 4-substituted phenyl with CH(R¹)–C(=O)–R¹⁵ group, and D-CH₂- at para position]

| Example No. | D | R¹ | R¹⁵ | Yield (% of theory) | R_f (solvent) | Melting point (° C.) | MS(*) (relative intensity) |
|---|---|---|---|---|---|---|---|
| 3 | 1-methylindol-3-yl | (R&S) cHept | (S)-NHMe-CH(Ph)-CH₂OH | 75 | 0.69 (L) | 170 | 481 (100%) |
| 4 | 1,2-dimethylindol-3-yl | (R&S) cHept | (S)-NHMe-CH(Ph)-CH₂OH | 76 | 0.71 (L) | 163 | 495 (100%) |
| 5 | 1,2,3-trimethylindol-? (1,2-diMe, 3-Me indole) | (R&S) cPent | (S)-NHMe-CH(Ph)-CH₂OH | 57 | | | 481 (80%) 480 (100%) |
| 6 | 1,2,3-trimethylindole | (dia A) cPent | (S)-NHMe-CH(Ph)-CH₂OH | | 0.37 (J) | 185 | |
| 7 | 1,2,3-trimethylindole | (dia B) cPent | (S)-NHMe-CH(Ph)-CH₂OH | | 0.23 (J) | 182 | |
| 8 | 1,2,3-trimethylindole | (R&S) cHex | (S)-NHMe-CH(Ph)-CH₂OH | 72 | 0.58 (J) | 180–82 | 494 (100%) |
| 9 | 1,2,3-trimethylindole | (dia A) cHex | (S)-NHMe-CH(Ph)-CH₂OH | | 0.54 (K) | 198 | |

TABLE 1-continued
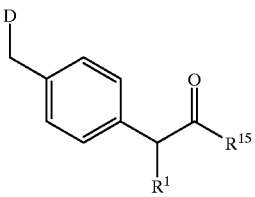
| Example No. | D | R¹ | R¹⁵ | Yield (% of theory) | R_f (solvent) | Melting point (° C.) | MS(*) (relative intensity) |
|---|---|---|---|---|---|---|---|
| 10 | 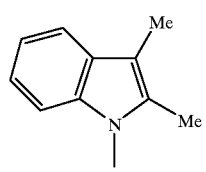 | (dia B) cHex | 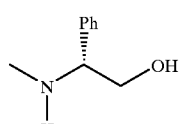 | | 0.39 (K) | 204 | |
| 11 | 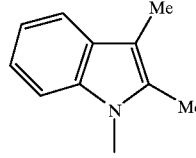 | (R&S) cHex | 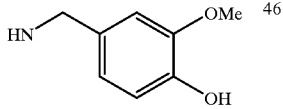 | 46 | 0.37 (J) | 98 (Foam) | 510 (100%) |
| 12 | 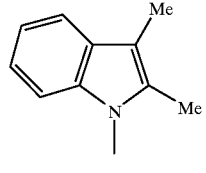 | (dia A) cHex | 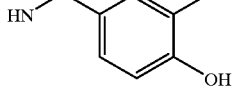 | | | 195–96 | |
| 13 | 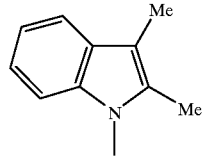 | (dia B) cHex | 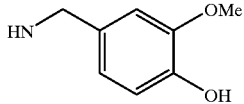 | | | 195–96 | |
| 14 | 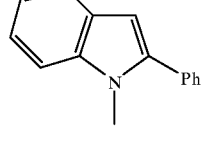 | (dia A) cPent | 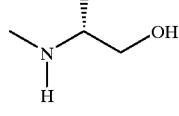 | 11 | 0.60 (K) | 183–85 | 529 (100%), 528 (80%) |
| 15 | 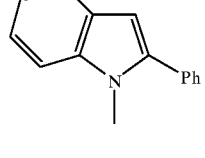 | (dia B) cPent | 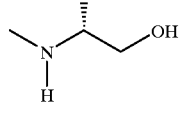 | 5 | 0.45 (K) | | 529 (100%), 528 (80%) |
| 16 | 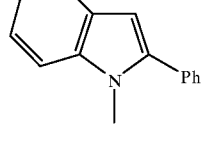 | (R&S) cHept | 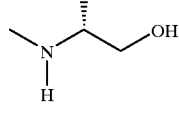 | 70 | 0.54 (K) | 182–86 | 557 (100%) |

TABLE 1-continued
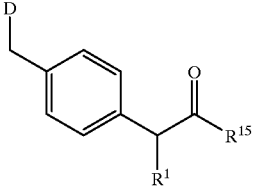
| Example No. | D | R¹ | R¹⁵ | Yield (% of theory) | $R_f$ (solvent) | Melting point (° C.) | MS(*) (relative intensity) |
|---|---|---|---|---|---|---|---|
| 17 | 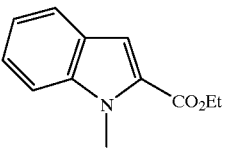 | (R&S) cPent | 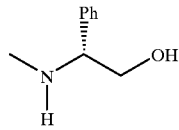 | 82 | | 118 | 525 (100%), 171 (100%) |
| 18 | 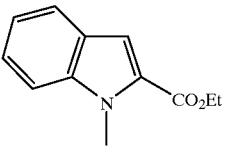 | (dia A) cPent | 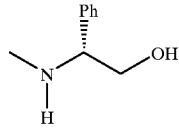 | | 0.54 (K) | | |
| 19 | 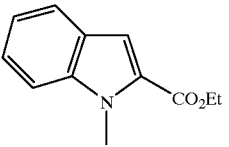 | (dia B) cPent | 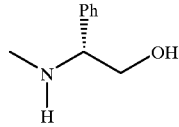 | | 0.44 (K) | | |
| 20 | 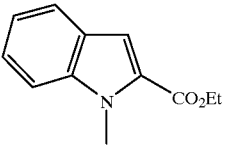 | (R&S) cHept | 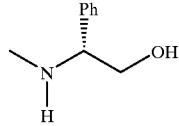 | 81 | 0.52 (K) | 178–81 | 553 (100%), 199 (100%) |
| 21 | 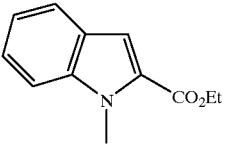 | (dia A) cHept | 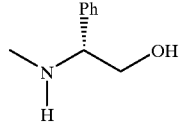 | | | 204 | |
| 22 | 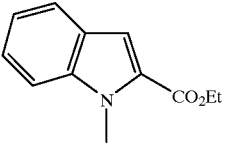 | (dia B) cHept | 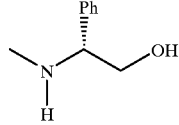 | | | 203 | |
| 23 | 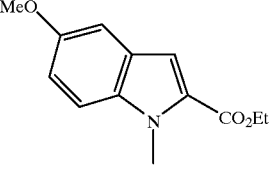 | (R&S) cPent | 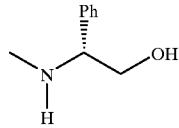 | 61 | | 116 | 555 (100%), 554 (90%) |

TABLE 1-continued

[Structure: 4-(CH2-D)-phenyl-CH(R1)-C(=O)-R15]

| Example No. | D | R1 | R15 | Yield (% of theory) | Rf (solvent) | Melting point (° C.) | MS(*) (relative intensity) |
|---|---|---|---|---|---|---|---|
| 24 | 5-MeO-1-Me-indole-2-CO2Et | (dia A) cPent | MeNH-CH(Ph)-CH2OH | | 0.47 (K) | | |
| 25 | 5-MeO-1-Me-indole-2-CO2Et | (dia B) cPent | MeNH-CH(Ph)-CH2OH | | 0.38 (K) | | |
| 26 | 5-Cl-1-Me-indole-2-CO2Et | (R&S) cPent | MeNH-CH(Ph)-CH2OH | 83 | | 158 | 559 (60%), 171 (100%) |
| 27 | 5-Cl-1-Me-indole-2-CO2Et | (dia A) cPent | MeNH-CH(Ph)-CH2OH | | 0.48 (K) | 162–65 | |
| 28 | 5-Cl-1-Me-indole-2-CO2Et | (dia B) cPent | MeNH-CH(Ph)-CH2OH | | 0.38 (K) | 191–93 | |
| 29 | 1,3-diMe-indole | (R&S) cHept | MeNH-CH(Ph)-CH2OH | 85 | 0.73 (L) | 171 | #494 (100%) |

TABLE 1-continued
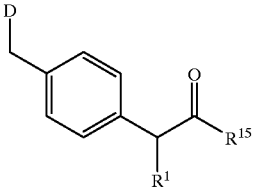
| Example No. | D | R[1] | R[15] | Yield (% of theory) | R_f (solvent) | Melting point (° C.) | MS(*) (relative intensity) |
|---|---|---|---|---|---|---|---|
| 30 | 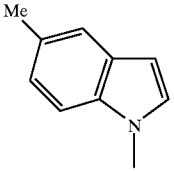 Me | (R&S) cPent | 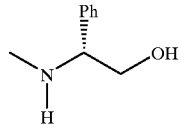 | 50 | 0.53 (K) | 155–61 | 467 (100%), 466 (80%) |
| 31 | 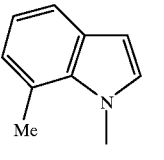 Me | (R&S) cPent | 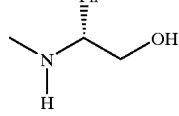 | 78 | 0.46 (K) | 186–90 | 467 (100%), 466 (80%) |
| 32 | 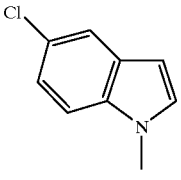 Cl | (R&S) cHept | 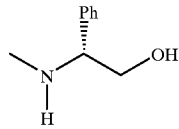 | 66 | 0.47 (K) | 153–55 | 515 (100%), 164 (80%) |
| 33 | 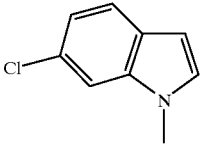 Cl | (R&S) cPent | 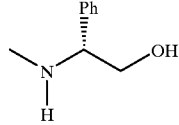 | 38 | 0.59 (K) | 170–75 | 487 (100%) |
| 34 | 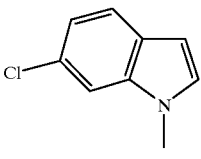 Cl | (dia A) cPent | 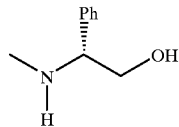 | | | 160–62 | |
| 35 | 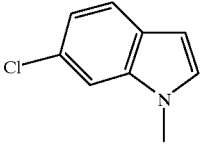 Cl | (dia B) cPent | 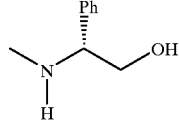 | | | 204–05 | |
| 36 | 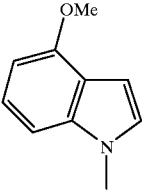 OMe | (R&S) cPent | 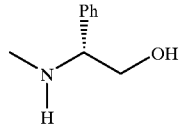 | 71 | 0.52 (K) | 173–76 | 482 (100%) |

TABLE 1-continued

| Example No. | D | R¹ | R¹⁵ | Yield (% of theory) | R_f (solvent) | Melting point (° C.) | MS(*) (relative intensity) |
|---|---|---|---|---|---|---|---|
| 37 | 4-OMe-1-Me-indol-3-yl | (dia A) cPent | N-Me, CH(Ph)CH₂OH | | | 183–85 | |
| 38 | 4-OMe-1-Me-indol-3-yl | (dia B) cPent | N-Me, CH(Ph)CH₂OH | | | 200–03 | |
| 39 | 5-MeO-1-Me-indol-3-yl | (R&S) cHept | N-Me, CH(Ph)CH₂OH | 78 | 0.55 (K) | 163–68 | 511 (80%), 510 (100%) |
| 40 | 1-Me-benzimidazol-2-yl | (R&S) cHept | N-Me, CH(Ph)CH₂OH | 86 | 0.25 (K) | 108 (Foam) | #482 (100%) |
| 41 | 1,2-diMe-benzimidazol-2-yl | (R&S) cHept | N-Me, CH(Ph)CH₂OH | 69 | 0.03 (K) | 110 (Foam) | #496 (100%) |
| 42 | 4,6-diCl-1,2-diMe-benzimidazol-2-yl | (R&S) cPent | N-Me, CH(Ph)CH₂OH | 54 | 0.28 (K) | 230–33 | 538 (70%), 536 (100%) |
| 43 | 4,6-diCl-1,2-diMe-benzimidazol-2-yl | (dia A) cPent | N-Me, CH(Ph)CH₂OH | | | | |

TABLE 1-continued

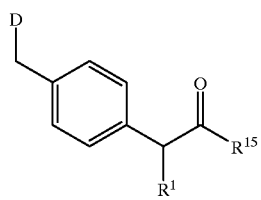

| Example No. | D | R[1] | R[15] | Yield (% of theory) | R_f (solvent) | Melting point (° C.) | MS(*) (relative intensity) |
|---|---|---|---|---|---|---|---|
| 44 | 4,6-dichloro-2-Me-1-Me-benzimidazole | (dia B) cPent | N-Me, Ph, CH2OH | | | >220 | |
| 45 | 2-iPr-1-Me-benzimidazole | (R&S) cPent | N-Me, Ph, CH2OH | 83 | 0.32 (K) | 93 | 496 (100%) |
| 46 | 2-nBu-1-Me-benzimidazole | (R&S) cPent | N-Me, Ph, CH2OH | 88 | 0.52 (L) | | |
| 47 | 2-nBu-1-Me-benzimidazole | (dia A) cPent | N-Me, Ph, CH2OH | | 0.52 (L) | | |
| 48 | 2-nBu-1-Me-benzimidazole | (dia B) cPent | N-Me, Ph, CH2OH | | 0.52 (L) | | |
| 49 | 2-tBu-1-Me-benzimidazole | (R&S) cPent | N-Me, Ph, CH2OH | 76 | 0.37 (K) | 104 (Foam) | 510 (100%), 154 (60%) |
| 50 | 2-cHex-1-Me-benzimidazole | (R&S) cPent | N-Me, Ph, CH2OH | 90 | 0.52 (K) | 100 (Foam) | 536 (100%), 105 (55%) |
| 51 | 4-Me-2-nPr-1-Me-benzimidazole | (R&S) cPent | N-Me, Ph, CH2OH | 54 | 0.47 (L) | | 510 (100%) |

TABLE 1-continued

| Example No. | D | R¹ | R¹⁵ | Yield (% of theory) | $R_f$ (solvent) | Melting point (° C.) | MS(*) (relative intensity) |
|---|---|---|---|---|---|---|---|
| 52 | 4-Me, 1-Me, 2-nPr benzimidazole | (dia A) cPent | Ph, MeNH-CH-CH₂OH | | 0.47 (L) | | |
| 53 | 4-Me, 1-Me, 2-nPr benzimidazole | (dia B) cPent | Ph, MeNH-CH-CH₂OH | | 0.43 (L) | | |
| 54 | 1-Me, 2-Ph benzimidazole | (R&S) cPent | Ph, MeNH-CH-CH₂OH | 99 | 0.54 (L) | | 530 (100%) |
| 55 | 1-Me, 2-Ph benzimidazole | (dia A) cPent | Ph, MeNH-CH-CH₂OH | | 0.54 (L) | | |
| 56 | 1-Me, 2-Ph benzimidazole | (dia B) cPent | Ph, MeNH-CH-CH₂OH | | 0.50 (L) | | |
| 57 | 1-Me, 2-Ph benzimidazole | (R&S) cHept | Ph, MeNH-CH-CH₂OH | 41 | 0.15 (U) | amorphous | 558 (100%) |
| 58 | 1-Me, 2-Ph benzimidazole | (dia A) cHept | Ph, MeNH-CH-CH₂OH | | | 191–2 | |
| 59 | 1-Me, 2-Ph benzimidazole | (dia B) cHept | Ph, MeNH-CH-CH₂OH | | | 211–2 | |

TABLE 1-continued
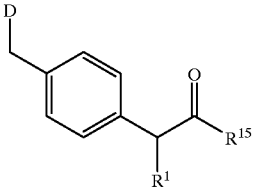
| Example No. | D | R¹ | R¹⁵ | Yield (% of theory) | $R_f$ (solvent) | Melting point (° C.) | MS(*) (relative intensity) |
|---|---|---|---|---|---|---|---|
| 60 | 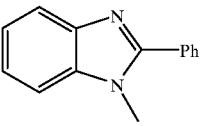 | (R&S) cHept | 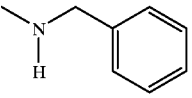 | 56 | 0.31 (U) | amorphous | 426 (100%) |
| 61 | 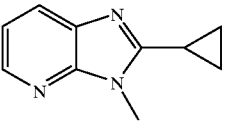 | (R&S) cPent | 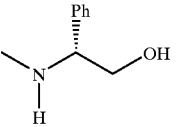 | 65 | 0.26 (K) | | 495 (100%) |
| 62 | 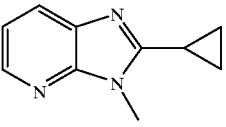 | (dia A) cPent | 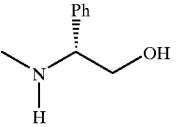 | | | 172 | |
| 63 | 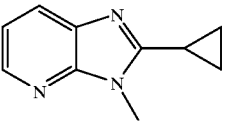 | (dia B) cPent | 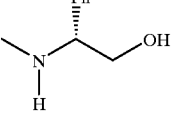 | | | 213 | |
| 64 | 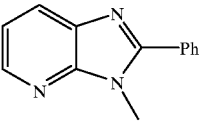 | (R&S) cPent | 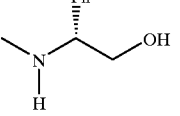 | 86 | 0.23 (K) | | 531 (100%) |
| 65 | 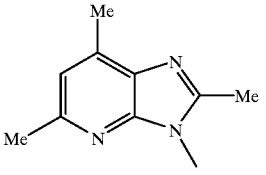 | (R&S) cPent | 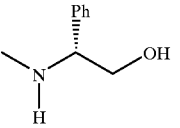 | 75 | | | 497 (100%) |
| 66 | 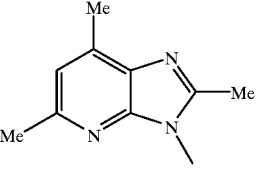 | (dia A) cPent | 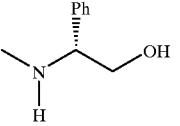 | | 0.20 (K) | 106–108 (Foam) | |
| 67 | 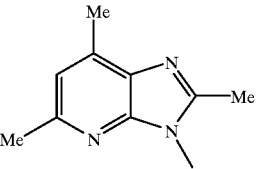 | (dia B) cPent | 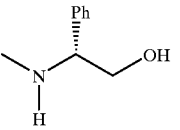 | | 0.16 (K) | 234 | |

TABLE 1-continued

| Example No. | D | R¹ | R¹⁵ | Yield (% of theory) | R_f (solvent) | Melting point (° C.) | MS(*) (relative intensity) |
|---|---|---|---|---|---|---|---|
| 68 | 2,5,7-trimethyl-3H-imidazo[4,5-b]pyridine (N-Me) | (R&S) cHex | (S)-2-(methylamino)-2-phenylethanol | | | | 511 (100%) |
| 69 | 2-cyclopropyl-5,7-dimethyl-3H-imidazo[4,5-b]pyridine (N-Me) | (R&S) cPent | (S)-2-(methylamino)-2-phenylethanol | 47 | 0.47 (K) | 186 | 523 (60%), 55 (100%) |
| 70 | 2-benzyl-5,7-dimethyl-3H-imidazo[4,5-b]pyridine (N-Me) | (R&S) cPent | (S)-2-(methylamino)-2-phenylethanol | 76 | 0.60 (K) | 100 (Foam) | #573 (100%) |
| 71 | 2-benzyl-5,7-dimethyl-3H-imidazo[4,5-b]pyridine (N-Me) | (dia A) cPent | (S)-2-(methylamino)-2-phenylethanol | | 0.41 (K) | 100 | |
| 72 | 2-benzyl-5,7-dimethyl-3H-imidazo[4,5-b]pyridine (N-Me) | (dia B) cPent | (S)-2-(methylamino)-2-phenylethanol | | 0.35 (K) | 150 | |
| 73 | 5,7-dimethyl-2-phenyl-3H-imidazo[4,5-b]pyridine (N-Me) | (R&S) cPent | (S)-2-(methylamino)-2-phenylethanol | 72 | 0.44 (K) | 210 | 559 (100%) |

TABLE 1-continued

[Structure: 4-(D-CH2)-phenyl-CH(R1)-C(=O)-R15]

| Example No. | D | R1 | R15 | Yield (% of theory) | R_f (solvent) | Melting point (° C.) | MS(*) (relative intensity) |
|---|---|---|---|---|---|---|---|
| 74 | 4,6-dimethyl-2-phenyl-3-methyl-3H-imidazo[4,5-b]pyridin-3-yl (Me, Me, Ph, N-Me) | (dia A) cPent | NHMe-CH(Ph)-CH2OH | | | | |
| 75 | 4,6-dimethyl-2-phenyl-3-methyl-3H-imidazo[4,5-b]pyridin-3-yl | (dia B) cPent | NHMe-CH(Ph)-CH2OH | | | | |
| 76 | 4,6-bis(trifluoromethyl)-1,2-dimethyl-1H-benzimidazol-1-yl | (R&S) cPent | NHMe-CH(Ph)-CH2OH | 82 | 210–12 | | 604 (60%), 105 (100%) |
| 77 | 4,6-bis(trifluoromethyl)-1,2-dimethyl-1H-benzimidazol-1-yl | (dia A) cPent | NHMe-CH(Ph)-CH2OH | | | 229 | |
| 78 | 4,6-bis(trifluoromethyl)-1,2-dimethyl-1H-benzimidazol-1-yl | (dia B) cPent | NHMe-CH(Ph)-CH2OH | | | 212 | |

We claim:
1. A benzimidazolyl-substituted phenylacetic acid compound of the formula:

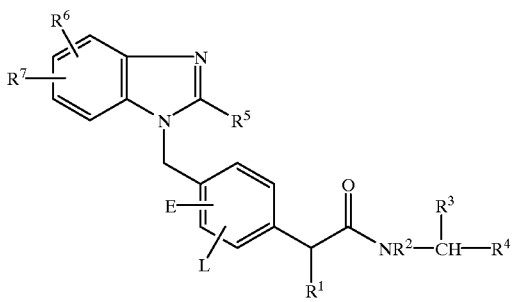

in which
R$^6$ and R$^7$ are identical or different and represent hydrogen, trifluoromethyl, halogen, or straight-chain or branched alkyl or alkoxy having in each case up to 6 carbon atoms;
R$^5$ represents hydrogen, cycloalkyl having 3 to 6 carbon atoms, phenyl, straight-chain or branched alkoxycarbonyl having up to 6 carbon atoms, or straight-chain or branched alkyl having up to 6 carbon atoms, which alkyl is optionally substituted by halogen;
E and L are identical or different and represent hydrogen, halogen, trifluoromethyl, hydroxyl, or carboxyl, or represent straight-chain or branched alkyl, alkoxy or alkoxycarbonyl having in each case up to 6 carbon atoms;
R$^1$ represents cycloalkyl having 3 to 10 carbon atoms, straight-chain or branched alkyl having 1 to 10 carbon atoms, or phenyl, which phenyl is optionally substituted once or twice by identical or different substituents independently selected from the group consisting of halogen, cyano, hydroxyl, and straight-chain or branched alkyl or alkoxy having in each case up to 4 carbon atoms;
R$^2$ represents hydrogen or straight-chain or branched alkyl having up to 3 carbon atoms;
R$^3$ represents hydrogen, straight-chain or branched alkyl having up to 5 carbon atoms, cycloalkyl having 3 to 7 carbon atoms, or phenyl, which phenyl is optionally substituted one to three times by identical or different substituents independently selected from the group consisting of halogen, nitro, phenyl, hydroxyl, or straight-chain or branched alkyl or alkoxy having up to 6 carbon atoms;
R$^4$ represents hydrogen, a group of the formula —CH$_2$—OH, or a group of the formula —CH$_2$—O—CO—R$^{12}$;
wherein
R$^{12}$ represents hydrogen, straight-chain or branched alkyl having up to 8 carbon atoms, or phenyl, which phenyl is optionally substituted one to three times by identical or different substituents independently selected from the group consisting of halogen, hydroxyl, cyano, or straight-chain or branched alkyl or alkoxy having in each case up to 4 carbon atoms;
or a salt thereof;
with the proviso that if R$^1$=cyclopentyl, R$^2$=hydrogen, R$^3$=phenyl, R$^4$=CH$_2$OH, and E, L, R$^6$ and R$^7$=hydrogen, then R$^5$≠hydrogen, n-butyl or phenyl.
2. A benzimidazolyl-substituted phenylacetic acid compound according to claim 1, in which
R$^6$ and R$^7$ are identical or different and represent hydrogen, trifluoromethyl, fluorine, chlorine, bromine, or straight-chain or branched alkyl or alkoxy having in each case up to 5 carbon atoms;
R$^5$ represents hydrogen, cyclopropyl, cyclopentyl, cyclohexyl, phenyl, straight-chain or branched alkoxycarbonyl having up to 5 carbon atoms, or straight-chain or branched alkyl having up to 5 carbon atoms, which alkyl is optionally substituted by fluorine, chlorine or bromine;
E and L are identical or different and represent hydrogen, fluorine, chlorine, bromine, trifluoromethyl, or hydroxyl, or represent straight-chain or branched alkyl or alkoxy having in each case up to 4 carbon atoms;
R$^1$ represents cyclobutyl, cyclopentyl, cyclohexyl, cycloheptyl, cyclooctyl, straight-chain or branched alkyl having 1 to 7 carbon atoms, or phenyl, which phenyl is optionally substituted once or twice by identical or different substituents independently selected from the group consisting of fluorine, chlorine, bromine, cyano, hydroxyl, and straight-chain or branched alkyl or alkoxy having in each case up to 3 carbon atoms;
R$^2$ represents hydrogen or methyl;
R$^3$ represents hydrogen, straight-chain or branched alkyl having up to 4 carbon atoms, cyclopropyl, cyclopentyl, cyclohexyl, or phenyl, which phenyl is optionally substituted one or two times by identical or different substituents independently selected from the group consisting of fluorine, chlorine, bromine, nitro, phenyl, hydroxyl, or straight-chain or branched alkyl or alkoxy having up to 4 carbon atoms;
R$^4$ represents hydrogen, a group of the formula —CH$_2$—OH, or a group of the formula —CH$_2$—O—CO—R$^2$;
wherein
R$^{12}$ represents hydrogen, straight-chain or branched alkyl having up to 6 carbon atoms, or phenyl, which phenyl is optionally substituted one or two times by identical or different substituents independently selected from the group consisting of fluorine, chlorine, bromine, hydroxyl, cyano, or straight-chain or branched alkyl or alkoxy having in each case up to 3 carbon atoms;
or a salt thereof;
with the proviso that if R$^1$=cyclopentyl, R$^2$=hydrogen, R$^3$=phenyl, R$^4$=CH$_2$OH, and E, L, R$^6$ and R$^7$=hydrogen, then R$^5$≠hydrogen, n-butyl or phenyl.
3. A benzimidazolyl-substituted phenylacetic acid compound according to claim 2, in which
R$^6$ and R$^7$ are identical or different and represent hydrogen, trifluoromethyl, chlorine, or straight-chain or branched alkyl or alkoxy having in each case up to 4 carbon atoms;
R$^5$ represents hydrogen, cyclopropyl, cyclopentyl, cyclohexyl, phenyl, straight-chain or branched alkoxycarbonyl having up to 4 carbon atoms, or straight-chain or branched alkyl having up to 4 carbon atoms, which alkyl is optionally substituted by chlorine;
E and L are identical or different and represent hydrogen, fluorine, chlorine, bromine, or trifluoromethyl;
R$^1$ represents cyclopentyl, cyclohexyl, cycloheptyl, cyclooctyl, straight-chain or branched alkyl having 1 to 6 carbon atoms, or phenyl, which phenyl is optionally substituted once or twice by identical or different substituents independently selected from the group consisting of fluorine, chlorine, cyano, hydroxyl, methyl and methoxy;

$R^2$ represents hydrogen or methyl;

$R^3$ represents hydrogen, straight-chain or branched alkyl having up to 3 carbon atoms, cyclopropyl, cyclopentyl, cyclohexyl, or phenyl, which phenyl is optionally substituted one or two times by identical or different substituents independently selected from the group consisting of fluorine, chlorine, bromine, nitro, phenyl, hydroxyl, or straight-chain or branched alkyl or alkoxy having up to 3 carbon atoms;

$R^4$ represents hydrogen, a group of the formula —CH$_2$—OH, or a group of the formula —CH$_2$—O—CO—$R^{12}$;

wherein $R^{12}$ represents hydrogen, straight-chain or branched alkyl having up to 6 carbon atoms, or phenyl, which phenyl is optionally substituted one or two times by identical or different substituents independently selected from the group consisting of fluorine, chlorine, bromine, hydroxyl, cyano, methyl and methoxy;

or a salt thereof;

with the proviso that if $R^1$=cyclopentyl, $R^2$=hydrogen, $R^3$=phenyl, $R^4$=CH$_2$OH, and E, L, $R^6$ and $R^7$=hydrogen, then $R^5 \neq$hydrogen, n-butyl or phenyl.

4. The compound 2-(R)- and 2-(S)-2-[4-(2-propyl-1H-benzimidazol-1-ylmethyl)-phenyl]-2-cyclopentyl-aceticacid (2-(R)-2-phenyl-glycinol)-amide of the formula

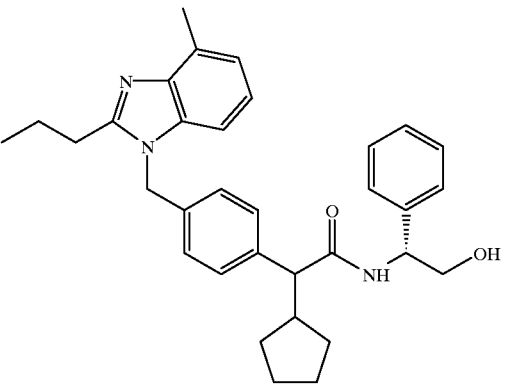

or a salt thereof.

5. A composition for the treatment of arteriosclerosis comprising an amount effective therefor of a compound or salt thereof according to claim 2 and a pharmacologically acceptable diluent.

6. A method for treating arteriosclerosis in a patient in need thereof which comprises administering to such patient an amount effective therefor of a compound or a salt thereof according to claim 3.

7. A composition for the treatment of arteriosclerosis comprising an amount effective therefor of a compound or salt thereof according to claim 4 and a pharmacologically acceptable diluent.

8. A method for treating arteriosclerosis in a patient in need thereof which comprises administering to such patient an amount effective therefor of a compound or a salt thereof according to claim 4.

* * * * *

UNITED STATES PATENT AND TRADEMARK OFFICE
CERTIFICATE OF CORRECTION

PATENT NO. : 6,034,115
DATED : March 7, 2000
INVENTOR(S) : Richard Connell, et al.

It is certified that error appears in the above-indentified patent and that said Letters Patent is hereby corrected as shown below:

Column 64, line 34, cancel "-$CH_2$-O-CO-$R^2$" and substitute -- -$CH_2$-O-CO-$R^{12}$--

Signed and Sealed this

Seventeenth Day of April, 2001

Attest:

NICHOLAS P. GODICI

Attesting Officer    Acting Director of the United States Patent and Trademark Office